(12) United States Patent
Kleyman et al.

(10) Patent No.: US 7,578,212 B2
(45) Date of Patent: Aug. 25, 2009

(54) FORCE AMPLIFIER

(76) Inventors: Gennady Kleyman, 1290 E. 19th St., Apt. 3A, Brooklyn, NY (US) 11230; Annaniy Berenshteyn, 98 Tanya Cir., Ocean, NJ (US) 07712

( * ) Notice: Subject to any disclaimer, the term of this patent is extended or adjusted under 35 U.S.C. 154(b) by 0 days.

(21) Appl. No.: 12/017,874

(22) Filed: Jan. 22, 2008

(65) Prior Publication Data

US 2009/0187151 A1 Jul. 23, 2009

(51) Int. Cl.
*F16H 25/20* (2006.01)
*F16H 37/16* (2006.01)

(52) U.S. Cl. .......................... 74/89.23; 74/110; 185/37; 254/98

(58) Field of Classification Search ................ 74/89.23, 74/89.35, 89.38, 89.45, 110, 22 R; 185/37, 185/39; 254/98
See application file for complete search history.

(56) References Cited

U.S. PATENT DOCUMENTS

| | | | |
|---|---|---|---|
| 2,800,804 A | * | 7/1957 | Olschwang ................ 74/89.35 |
| 3,967,377 A | * | 7/1976 | Wells .......................... 30/320 |
| 4,465,478 A | | 8/1984 | Sebelman |
| 5,342,304 A | | 8/1994 | Tacklind |
| 5,603,701 A | | 2/1997 | Fischer |
| 5,800,405 A | | 9/1998 | McPhee |
| 5,830,194 A | | 11/1998 | Anwar |
| 5,860,955 A | | 1/1999 | Wright |
| 6,110,151 A | | 8/2000 | Spool |
| 7,018,365 B2 | | 3/2006 | Strauss |
| 7,041,084 B2 | | 5/2006 | Fojtik |

* cited by examiner

*Primary Examiner*—William C Joyce
(74) *Attorney, Agent, or Firm*—The Farrell Law Firm, LLP

(57) ABSTRACT

A force amplifier has a guide track, a non-locking screw threadedly engaging the track to spirally move in response to an axial input force applied to the proximal end of the non-locking screw. The force amplifier includes a compliant component coupled to the non-locking screw by one end and to a self-locking screw by the other end. The compliant component is configured to transmit a torque generated by the non-locking screw to the self-locking screw, which is actuated to move spirally along the track while generating an axial output force greater than the input force.

8 Claims, 6 Drawing Sheets

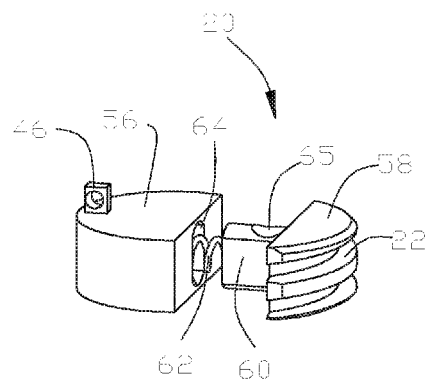
FIG.11
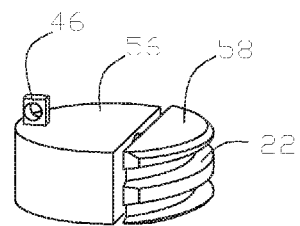
FIG.12
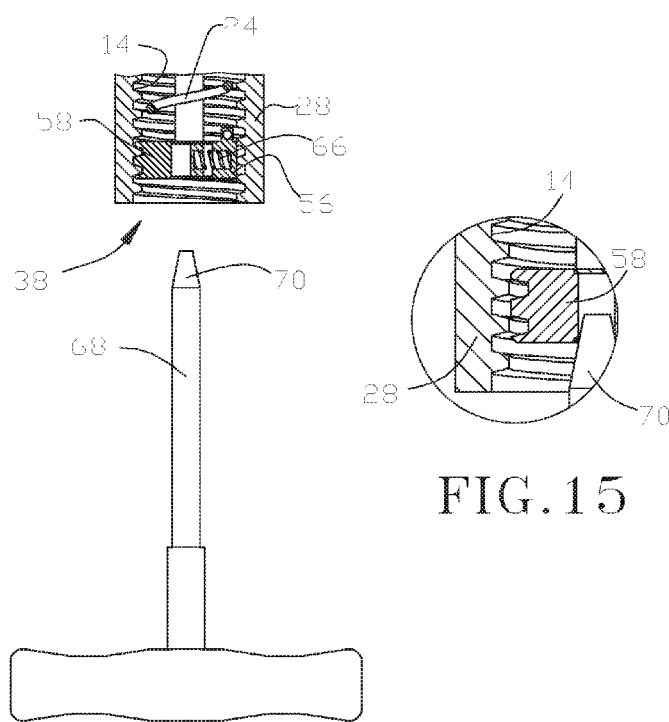
FIG.13
FIG.15
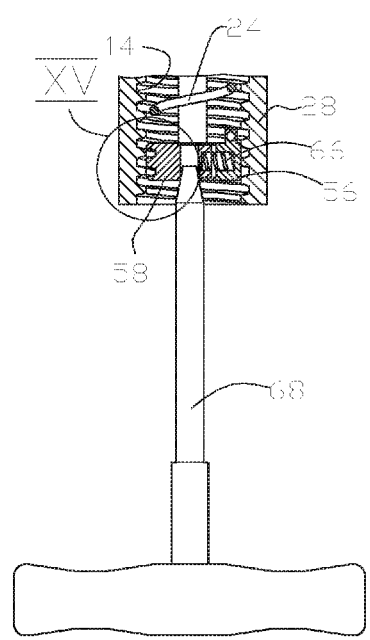
FIG.14

FORCE AMPLIFIER

This application is based on Disclosure Document NO. 607293 filed Oct. 13, 2006, the contents of which is incorporated herein by reference.

FIELD OF THE INVENTION

The invention relates to a force amplifier.

BACKGROUND OF THE INVENTION

Dispensing of sticky and/or viscous materials from a syringe requires the application of a significant force to the plunger of the syringe. Depending on the viscosity of the dispensed material and the amount of this material, the user may experience difficulties in generating and/or maintaining the necessary force for a required period of time. Consequently, inadequate force and/or fatigue, particularly when a need arises to use a syringe repetitively, can lead to undesirable, inaccurate results.

Conventional devices that amplify an input force typically are configured with a pistol-type handle having an attached lever which amplifies the force of the person's hand and applies it to the plunger of a syringe.

Regular syringes, those that do not have a force-amplification structure, are typically held by the user between the index and middle fingers whereas the thumb applies the force to the syringe plunger. When significant force is not required, such a syringe is associated with accurate aiming of the substance to be dispensed and full control of the dispensing, since the motion of the thumb coincides with the line of the plunger's movement.

During the use of a conventional force amplifying syringe, the line of movement of the plunger is located above the user's hand, and the distribution of substance from the syringe occurs when the user squeezes the lever of the syringe. This configuration does not allow accurate aiming of the substance and hampers dispensing, especially in applications where such substance delivery occurs in tight areas with limited visibility. These conditions can be encountered in numerous industries including, but not limited to, medical procedures, such bonding fractured bones or cementing ruptured spinal disks.

It is, therefore, desirable to provide a force amplifier configured to provide accurate dispensing of substance while not requiring the application of significant axial loads.

SUMMARY OF THE INVENTION

The present invention overcomes the above-described limitations of conventional devices and attains the above-described advantages by providing an apparatus utilizing a threaded non-locking screw and a threaded self-locking screw having respective lead angles, which differ from one another, and a compliant component capable of transmitting a torque from the non-locking screw to the self-locking screw. Depending on the lead angles and pitch diameters of the respective threads, the self-locking screw is displaceable at a distance shorter than that of the non-locking screw while generating an output force which is greater than an input force applied to the non-locking screw.

In a preferred aspect of the invention, the non-locking screw is a generally cylindrical component provided with a first thread which engages an upstream guide thread of a housing. The self-locking screw, which also has a circular cross-section, is configured with a second thread engaging a downstream guide thread of the housing. The threads of the non-locking screw and self-locking screw have respective lead angles $\lambda_1$ and $\lambda_2$, wherein $\lambda_1$ is greater than $\lambda_2$. The lead angle is defined between the tangent to a helix of the displaceable thread and the axial axis of the thread and can be calculated using Equation (1):

$$\tan \lambda = P/\pi D \tag{1}$$

where P is a thread pitch, i.e., the distance from a point on the thread to a corresponding point on the next thread measured parallel to the axis; and D is a pitch diameter of the thread, i.e., the diameter of the thread where the width of the thread equals to the width of the space between adjacent threads.

According to one aspect of the invention, the lead angle $\lambda_1$ of the first thread of the non-locking screw is substantially larger than the lead angle $\lambda_2$ of the second thread of the self-locking screw. The lead angle $\lambda_1$ of the non-locking screw's thread $\lambda$ prevents self-locking of the thread, i.e., when an axial force is applied to a screw, the screw moves in axial direction and at the same time follows the helix of the threaded hole, thus performing a spiral movement. Self-locking of a thread is determined by Equation (2) below; where f is a coefficient of friction between the thread of the screw and the thread of the hole; and $\lambda$-lead angle.

The lead angle $\lambda_2$ of the second tread of the non-locking screw must satisfy the condition that guaranties self-locking of the thread, i.e., the screw cannot move in axial direction when an axial force is applied to a screw and movement of the screw can occur only when a torque (rotational momentum) is applied to the screw. The condition for self-locking of a thread is provided by Equation (2):

$$f \geq P \cos \lambda / \pi D \tag{2}$$

In the present invention the self-locking screw does not allow a thrust load, when applied to the end of the screw, to create a torque; the screw is not movable unless a torque is applied. For example, a screw engaging a threaded cavity will not rotate, no matter how great an axial load is, with a self-locking screw. Conversely, a self-unlocking screw can rotate relative to the threaded cavity in response to a small axial force and, if the structure is displaced at a sufficient angle relative to a horizontal, the screw can move under the force of gravity.

The difference in the lead angles of the respective non-locking screw and follower provides for a relatively small input force applied to the actuator to be substantially amplified at the output of the self-locking screw. Numerically, the ratio between the output and input forces is proportional to the ratio between the lead angles of the respective first and second threads. As a consequence, the ratio between the axial distance covered by the respective non-locking screw and follower is inversely proportional to the ratio of the forces.

According to a further aspect of the invention, a compliant force transmitting component coupled by its opposite ends to the respective non-locking screw and follower is operative to transmit a torque generated by the non-locking screw to the self-locking screw. But for the compliant component, the rigidly coupled screws can only move until the self-locking screw locks against a threaded track along which the screws move. For example, when the lead angle ratio between the force amplifier and self-locking screw is 4 to 1 in terms of displacement, a single revolution of the non-locking screw relative to the threaded outer guide track translates in an axial distance covered by the non-locking screw of four times greater than the self-locking screw. If the force components were rigidly coupled to one another, they could move only as long as the tolerances of the structure would allow the follower to move. Clearly, for all practical purposes, the rigidly coupled force components would get edged immediately upon applying an axial thrust. The compliant component, thus, is operative to compensate for the differences in the distances covered by the force components in response to the axial thrust without having the self-locking screw wedged against the guide track.

BRIEF DESCRIPTION OF THE DRAWINGS

The above and other features and advantages of the disclosed force amplification apparatus will become more apparent from the following detailed description given in conjunction with the drawings, in which:

FIG. 11 is an exploded view of a locking component shown in an unlocked position and configured to prevent voluntary displacement of the actuator of the disclosed force amplifying apparatus to the initial position;

FIG. 12 shows the locking component shown in a locked position;

FIG. 13 illustrates a key component configured to operate the locking component of FIGS. 11 and 12;

FIG. 14 illustrates the opening of the locking component of FIGS. 11-12 by the key component of FIG. 13;

FIG. 15 is an enlarged view of a fragment "XV" of FIG. 14 illustrating the operation of the key component of FIGS. 13 and 14;

DETAILED DESCRIPTION OF THE PREFERRED EMBODIMENTS

Figure 1:
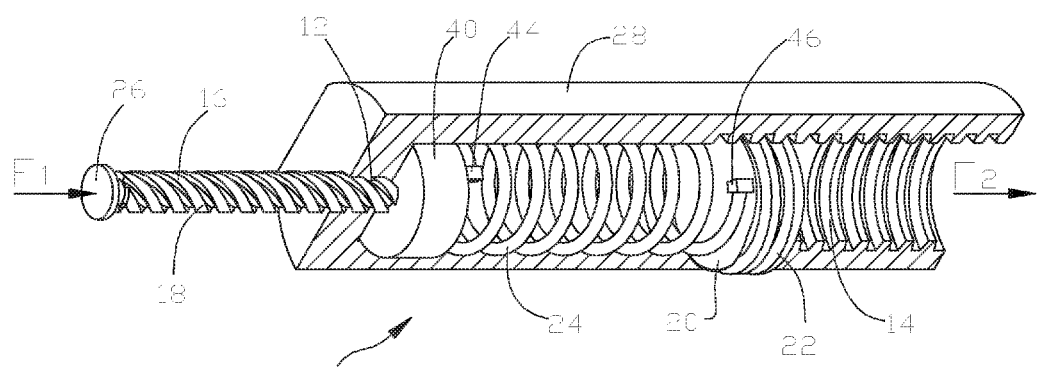
FIG. 1 is a cross-sectional view of the force amplification apparatus of the present invention with a substance delivery component removably attached thereto.

Reference will now be made in detail to the disclosed system. Wherever possible, same or similar reference numerals are used in the drawings and the description to refer to the same or like parts or steps. The drawings are in simplified form and are far from precise scale. For purposes of convenience and clarity only, the terms "connect," "couple," "combine" and similar terms with their inflectional morphemes do not necessarily denote direct and immediate connections, but also include connections through mediate elements or devices. The following detailed discloses a syringe; however, one of ordinary skills in the mechanical arts readily realizes that the disclosed structure can be utilized in a variety of technological fields requiring force amplification.

Figure 2A:
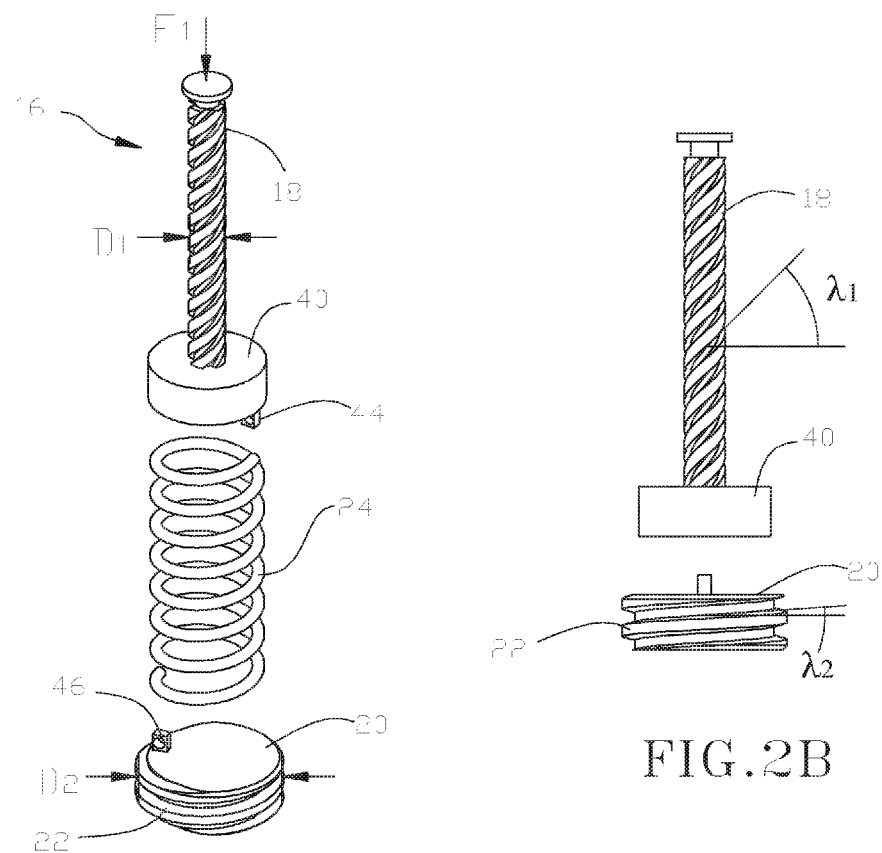
FIG. 2A is an exploded view of non-locking and self-locking screws of amplification apparatus of FIG. 1.
Figure 2B:
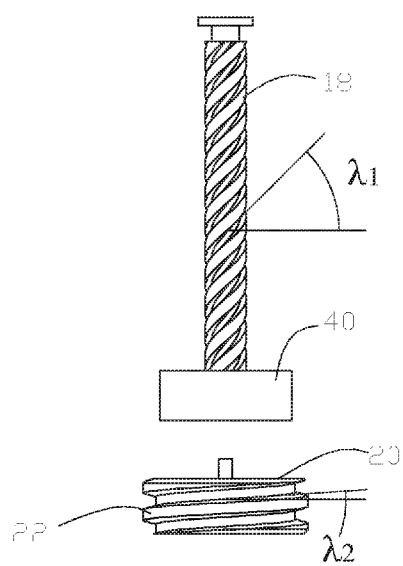
FIG. 2B is a side view of the non-locking and self-locking screws of FIG. 2A provided with respective lead angles.

Referring to FIGS. 1, 2A and 2B, a force amplifier 10 has a guide track 28 provided with first and second threaded regions 12 and 14, respectively. The amplifier 10 is further configured with a non-locking screw 16 having a first outer screw thread 18 engage first threaded region 12, and a self-locking screw 20 provided with a respective screw thread 22 engaging second threaded region 14.

Turning to FIGS. 2A and 2B, first and second screw threads 18 and 22 (FIG. 2B) have respective $\lambda_1$ and $\lambda_2$ lead angles dimensioned so that $\lambda_2$ is smaller than $\lambda_1$, wherein the lead angle is the angle that the tangent to a helix of the thread makes with the plane normal to the axis of the thread. The lead angles are selected so that non-locking screw 16 is operative to spirally move along the track in response to a thrust. In other words, when an axial force $F_1$ is applied to non-locking screw 16, it moves linearly and at the same time follows the helix of the threaded guide track, thus performing a spiral movement. On other hand, self-locking screw 20 (FIG. 2A) cannot move in response to the axial force, but is displaceable only when a torque (rotational momentum) is applied to this component.

The present invention allows the user to apply an insignificant thrust to the proximal end of non-locking screw 16 which, in response, starts rotating while linearly moving relative to first threaded region 12. In contrast, if one applied an insignificant axial load or thrust to self-locking screw 20, the latter would not rotate unless acted upon by a torque. Preferably $\lambda_2$ of self-locking screw's thread 22 is several times smaller than the lead angle $\lambda_2$ of non-locking screw's thread 18.

Referring again to FIG. 1 in addition to FIGS. 2A and 2B, to create conditions for actuating self-locking screw 20, a compliant component-compressible force transmitter 24 (FIGS. 1 and 2A) is coupled to non-locking screw 16 and self-locking screw 20 by its respective proximal and distal ends. The force transmitter 24 thus rotates while being linearly displaced by screw 16 in response to an input axial force $F_1$ which is applied to a proximal end 26 of non-locking screw 16. The rotational displacement of force transmitter 24 causes self-locking screw 20 to rotate and linearly move along a spiral trajectory relative to second threaded region 14 (FIG. 1) of the track. The selection of lead angles $\lambda_1$ and $\lambda_2$ (FIG. 2B) of respective screw threads 18 and 22 allows self-locking screw 20 to generate a substantially greater output force $F_2$ than input force $F_1$. Specifically, an $F_2/F_1$ ratio is directly proportional to a $\lambda_1/\lambda_2$ value and inversely proportional to a $D_2/D_1$ value, where $D_1$ and $D_2$ (FIG. 2A) are the pitch diameters of the first and second threads correspondently. Assuming equal pitch diameters and that lead angle $\lambda_1$ of thread 18 of non-locking screw 16 is, for instance, 50°, whereas lead angle $\lambda_2$ of thread 22 of self-locking screw 20 is 10°, apparatus 10 may produce an output forces $F_2=5F_1$ (50:10=5 times).

The following description relates to force amplifier 10 which is configured as being attachable a syringe. Since the compactness of a syringe is important for all practical consideration, the pitches of non-locking and self-locking screws 16 and 20, respectively, are selected so that thread 18 of non-locking pitch is smaller than that one of self-locking screw's thread 22. As well understood by one of ordinary mechanical skill, the pitch of respective threads 18 and 22, i.e., the axial distance between adjacent threaded grooves, may be equal or the former may be larger than the latter. However, this particular application of the disclosed force amplifier as a syringe simply illustrates further structural details and is not intended to be exclusive.

Figure 3:
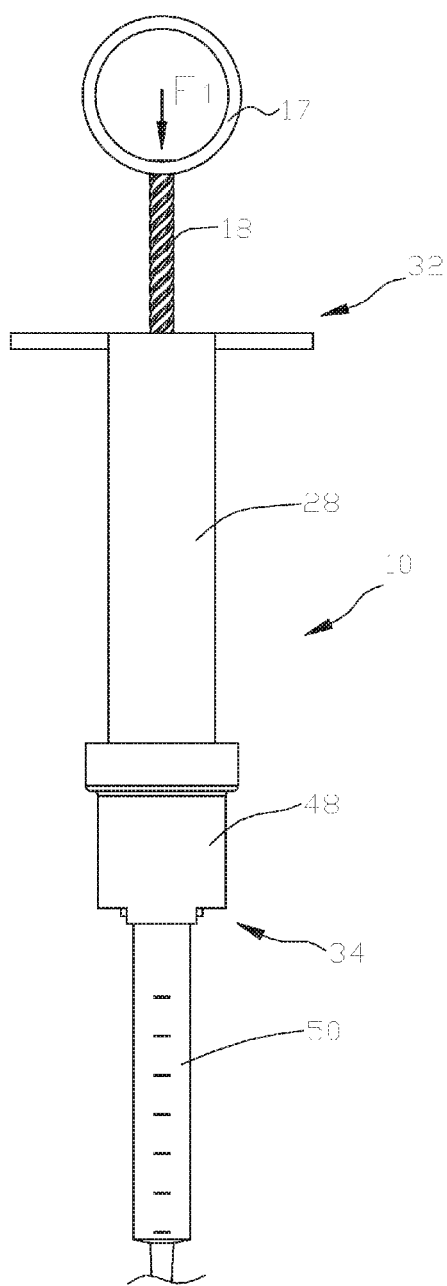
FIG. 3 is a side view of the force amplifier of FIG. 1.
Figure 4:
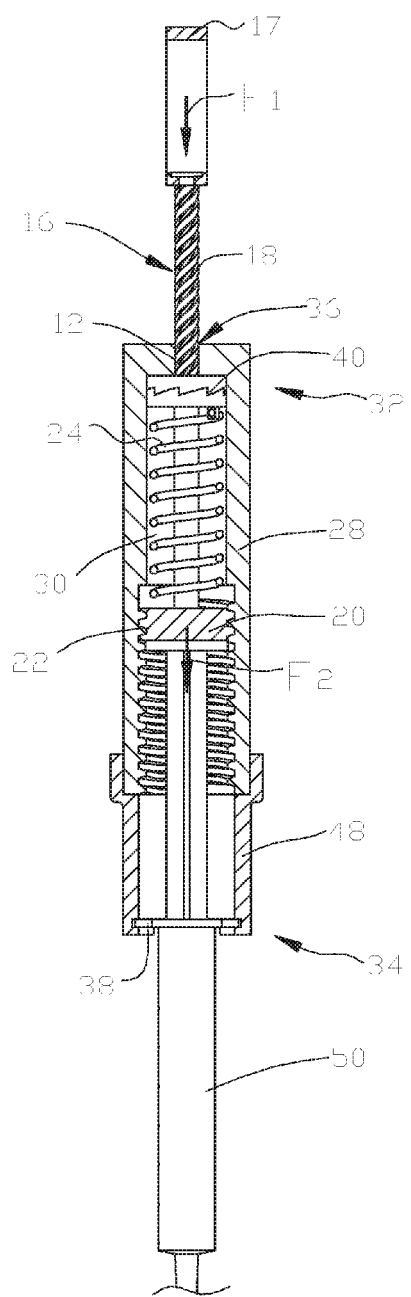
FIG. 4 is a cross-sectional side view of the apparatus of the present invention shown in an initial stage of the first working cycle.

Referring to FIGS. 3-4, force amplifier 10 is illustrated having a guide track 28 provided with an inner surface which delimits a hollow interior 30. Proximal and distal ends 32 and 34 of guide track 28 have respective inlet and outlet openings 36 and 38. The non-locking screw 16 includes a threaded plunger having first screw thread 18 which engages first threaded region 12 formed on the inner surface of inlet opening 36. The distal end 34 of screw 16, protruding into hollow exterior 30, is coupled to a ring 40 which, while rotating with the plunger, linearly moves along hollow interior 30.

The force transmitter 24 includes, for instance, a compression spring displaceably fixed to ring 40 and connected to bosses 44 and 46 at opposite ends thereof. The distal end of compressible force transmitter 24 engages boss 46 of self-locking screw 20, which has second screw thread 22.

Figure 5:
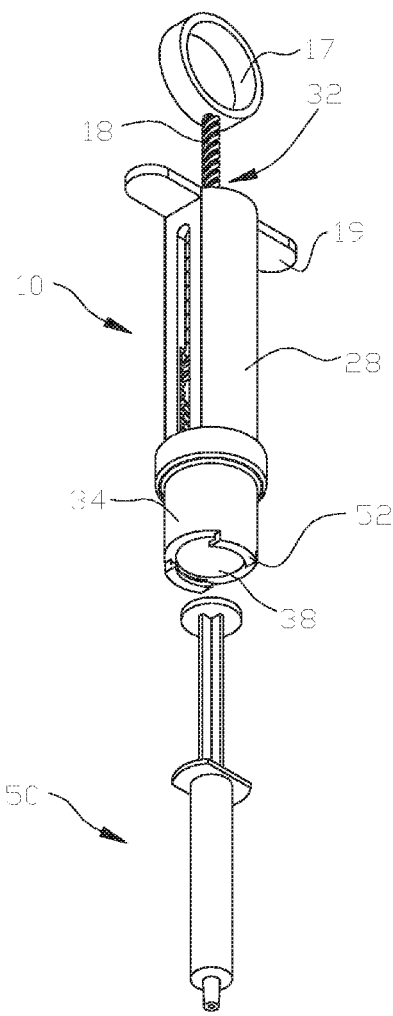
FIG. 5 is a view of the force amplification apparatus of FIG. 4 detached from the syringe.
Figure 6:
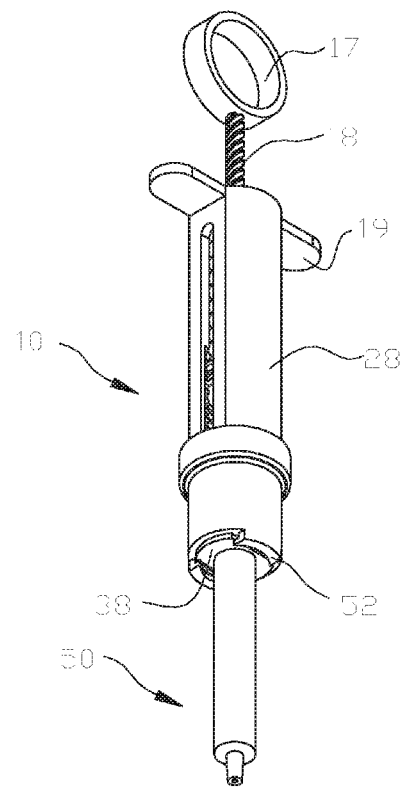
FIG. 6 is a perspective view of the assembled force amplification apparatus and syringe.

Referring to FIGS. 5, 6 in addition to FIGS. 3 and 4, outlet opening 38 of guide track 28 is preferably formed on a flange 48 coupled to guide track 28. The distal end of flange 48 has a receiving component, such as a bayonet connection 52, removably engaging the matching component of a syringe unit 50. Of course, all possible connections known in the art may be utilized within the scope of the disclosure. To simplify the operation of the syringe, proximal end 32 of the syringe preferably includes thumb enclosure 17 dimensioned to receive the user's thumb, whereas the middle and index finger can be firmly placed under a finger support 19. As illustrated, non-locking screw 16, guide track 28 and syringe unit 50 are all coaxial. Accordingly, force amplifier 10 has the desired aiming capability and requires substantially smaller forces applied by the user if compared to conventional force amplifiers.

Figure 7:
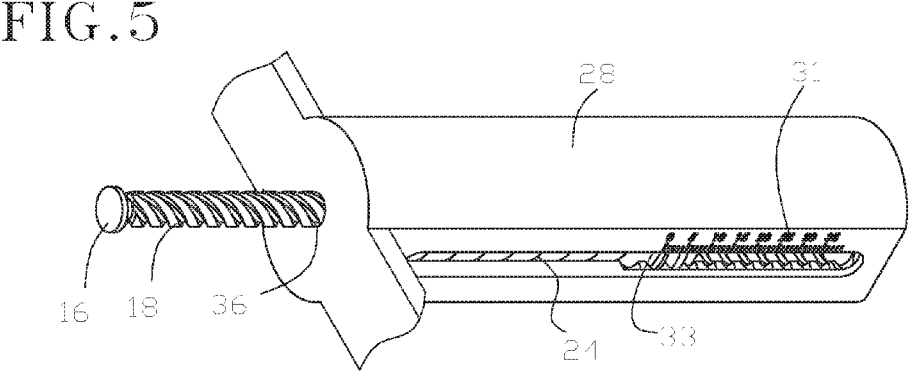
FIG. 7 is a side view showing a dosage-indicating scale.

Turning to FIG. 7, the volume of dispensed substance can be monitored by visually observing displacement of self-locking screw 20 through a slit 33 along a scale 31.

Figure 8:
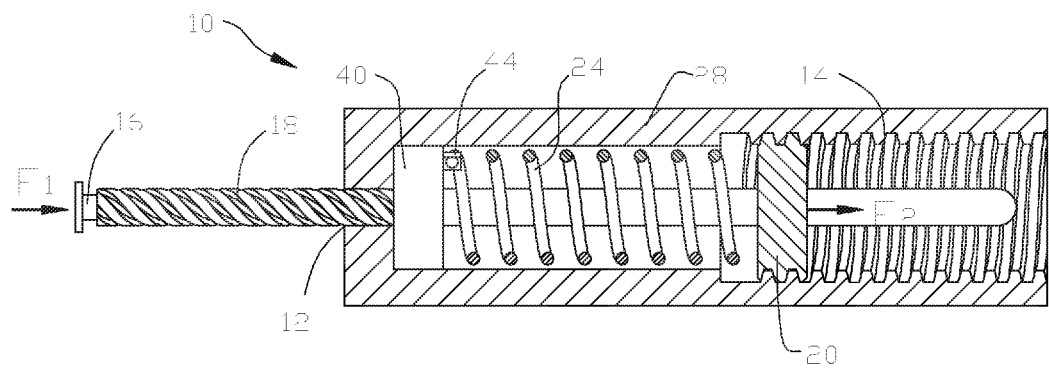
FIG. 8 is a cross-sectional side view of the apparatus of the present invention shown in the initial stage of a working cycle.
Figure 9:
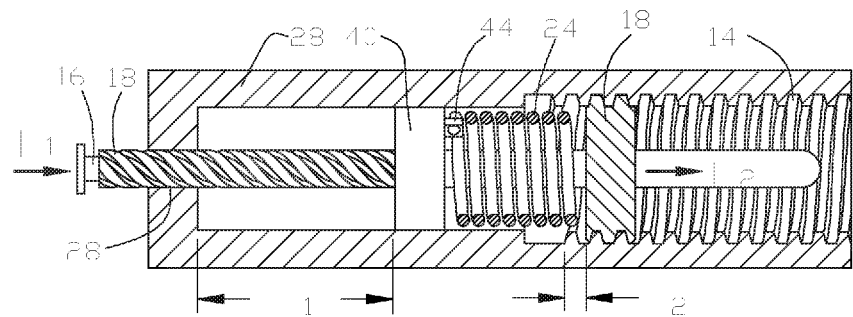
FIG. 9 is a cross-sectional side view of the disclosed apparatus shown in an intermediary stage of the working cycle corresponding to partial distribution of a substance to be delivered.
Figure 10:
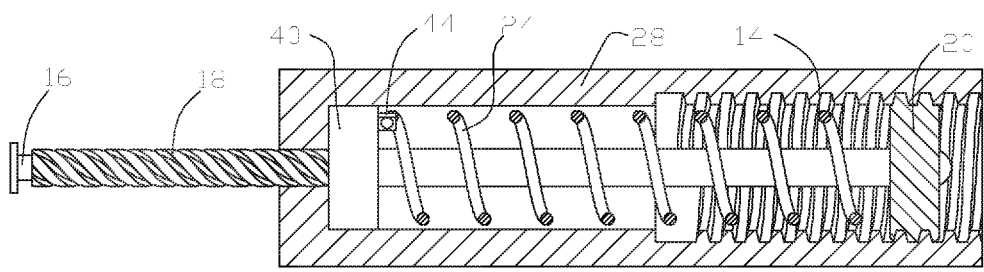
FIG. 10 is a cross-sectional side view of the disclosed apparatus illustrated in the final distributing stage of the working cycle.

FIGS. 8-10 illustrate the operation of force amplifier 10. In response to axial load or input force $F_1$, non-locking screw 16 starts rotating while linearly moving relative to first threaded region 12. The ring 40 fixed to the distal end of screw 16 follows the latter and simultaneously rotates and moves linearly towards distal end 34 of guide track 28 covering, for example, a distance $L_1$ (FIG. 9). The displacement of ring 40 causes actuation of force transmitter 24 which, while rotating, keeps compressing as long as axial input force $F_1$ is applied to the proximal end of non-locking screw 16. As a result, the distal end of transmitter 24 generates a compression force that rotatably actuates self-locking screw 20 which, while being linearly displaced at a distance $L_2$ (FIG. 9) substantially smaller than distance $L_1$, generates output force $F_2$. In response to output force $F_2$, the desirable volume of substance is dispensed via the syringe unit.

The distance $L_2/L_1$ is inversely proportional to the $F_2/F_1$ ratio. Accordingly, based on the example disclosed above, if F2 is 5 times greater than F1, and supposing that pitch diameters of screws 16 and 20 are equal, distance L2 is 5 times smaller than L1 After the user ceases the thrust into force, compression force transmitter 24 decompresses so that its proximal end along with ring 40 and non-locking screw 16 is displaced from an intermediary position (FIG. 9) to its initial position (FIG. 8). A further application of the input force would lead to displacing self-locking screw 20 to a final position thereof, as can be easily shown in FIG. 10. Once non-locking screw 16 completes the full stroke corresponding to a maximum compression of force transmitter 24, it is displaced back to its initial position due to the extension force generated by force transmitter 24. However, voluntary reverse displacement of self-locking screw 20 to the position shown in FIG. 8 is impossible and can only be accomplished based on the mechanism explained below.

FIGS. 11-15, in addition FIGS. 8-10, illustrate the configuration of self-locking screw 20 operating so that in a normal position, as shown in FIG. 8, it frictionally engages second threaded region 14 and in the final position shown in FIG. 10, screw 20 is operative to disengage the threaded region and slide back to the position shown in FIG. 8.

The self-locking screw 20 is configured with multiple segments 56 and 58, as shown in FIGS. 11-15. Segment 58 has a threaded circumference provided with second screw thread 22 which meshes with second threaded region 14 of guide track 28 (FIGS. 1 and 2). The segment 58 further has a generally T-shaped cross-section with an arm 60 extending from the inner side of segment 58. A resilient component 62 is braced between segments 56 and 58 respectively, and configured to bias the segments away from one another in normal and intermediary positions of self-locking screw 20, as illustrated in FIGS. 8 and 9, respectively. The resilient component 62 extends through an opening 64 (FIG. 11) of segment 56 and terminates within a passage 66 (FIG. 13, 14) extending through arm 60 of segment 58 transversely to opening 65 made in arm 60 for the reasons explained hereinbelow. The other segment 56 of self-locking screw 20 has a smooth circumference sliding along second threaded region 14 during displacement of self-locking screw 20.

When the actuator 16 reaches the end of its stroke, as shown in FIG. 13, self-locking screw 20 is located close to output opening 38 of guide track 28 (FIG. 13). Because of its configuration, self-locking screw 20 is locked and cannot voluntarily move back. The release of screw 20 from engagement with second threaded region 14 (FIG. 13) can be implemented in a variety of ways. Shown only as an example, a kit including the disclosed syringe, may have a key 68, as shown in FIGS. 13 and 14, dimensioned to penetrate outlet opening 38. The tip 70 of key 68 has a coned shape narrowing towards the apex of the tip. When the user drives tip 70 into outlet opening 38 with a force exceeding the biasing force of resilient component 62, segments 36 and 58, respectively, move towards one another in a release position, as shown in FIGS. 11 and 14. As a consequence, second screw thread 22 disengages second threaded region 14 of guide track 28 and slides back along the latter under the pulling force of force transmitter 24.

Figure 16:
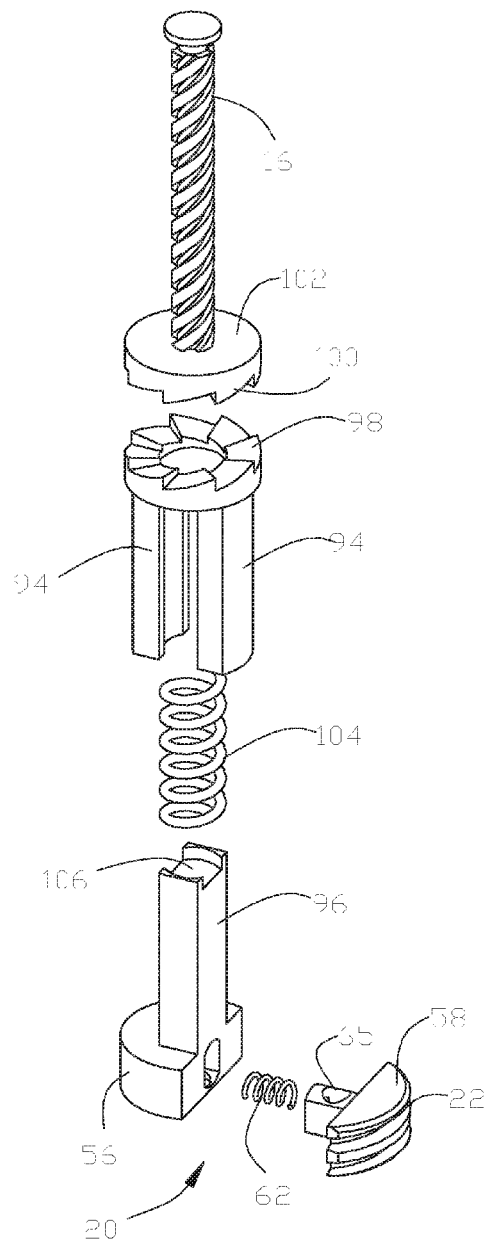
FIG. 16 is an exploded view of a further embodiment of the present invention configured with a telescopic force-transmitting component.
Figure 17:
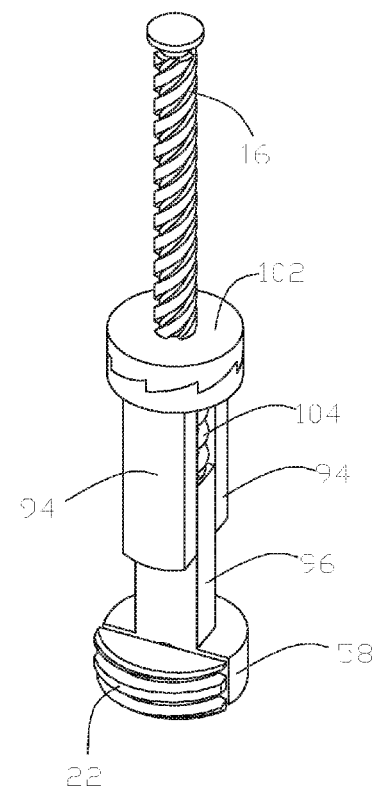
FIG. 17 is a side view of the embodiment of FIG. 16.

FIGS. 16 and 17 illustrate a further embodiment of the disclosed apparatus having a compliant component configured with a telescopic structure. The disclosed device has a non-locking screw 16, a self-locking screw 20 configured with two displaceable segments 56 and 58, which are biased by a spring 62, as discussed above in reference to FIGS. 11-15. Instead of a single force-transmitting spring operative to compensate for the difference in the lead angles and, thus, for the differences in the axial distances of the respective non-locking and self-locking screws, this embodiment of apparatus 10 features an outer element 94 and an inner element 96 coupled to respective non-locking screw 16 and self-locking screw 20. The inner and outer elements 96 and 94, respectively, are configured to axially slide relative to one another so as to transmit a thrust applied to non-locking screw 6 to an axial displacement of self-locking screw 74.

The proximal end of outer element 94 has a plurality of teeth 98 operative to mesh with complementarily-formed teeth 100 provided on distal end 102 of non-locking screw 16. The meshed arrays of teeth 98 and 100, respectively, define a ratchet mechanism allowing the teeth to engage one another in one rotational direction and freely move relative to one another on the opposite rotational direction. When non-locking screw 16 is axially and rotationally displaced in response to an axial thrust, teeth 100 mesh with teeth 98 so as to rotationally and axially actuate outer element 94. The distal end of outer element 94 is coupled to inner element 96 by a spring 104.

The inner element 96 has a pillar-like configuration provided with a nest 106 at its proximal end. The nest 106 is structured to receive and retain the distal end of spring 104. The spring 104 biases outer and inner elements 94 and 96, respectively, away from one another during a delivery stroke and provides reverse displacement of outer element 94 and reliable engagement between teeth 98 and 100 upon distribution of the desired dose of substance from the syringe. As readily understood by one or ordinary mechanical skill, elements 94 and 96 can be configured so that element 94 is an inner element while element 96 is a receptacle.

As described above, in a preferred embodiment, the force amplifier of the present invention operable couples to a standard syringe without exposing any part of the amplifier to the substance contained within the syringe, thereby providing an amplifier that can be reused with numerous syringes on a plurality of patients without concern of contamination.

Although shown and disclosed is what is believed to be the most practical and preferred embodiments, it is apparent that departures from the disclosed configurations and methods will suggest themselves to those skilled in the art and may be used without departing from the spirit and scope of the invention. Accordingly, the present invention is not restricted to the particular constructions described and illustrated, but should be construed to cohere with all modifications that may fall within the scope of the appended claims.

The invention claimed is:

1. A force amplifier comprising:
a guide track having first and second threaded regions;
a non-locking screw engaging the first threaded region to move relative to the track in response to an input force;
a compliant component having one end rotationally coupled to the non-locking screw to generate a torque at an opposite end thereof; and
a locking screw coupled to the opposite end of the compliant component and engaging the second threaded region so as to move in response to the torque to generate an axial output force greater than the input force.

2. The force amplifier of claim 1, wherein the non-locking and self-locking screws include respective first and second threads, the first and second threads having respective $\lambda 1$ and $\lambda 2$ angles.

3. The force amplifier of claim 2, wherein a ratio of output to input force is proportional to $\lambda_1/\lambda_2$.

4. The force amplifier of claim 3, wherein the non-locking and locking screws are axially displaced at respective first and second distances $L_1$ and $L_2$, wherein an $L_1/L_2$ ratio being proportional to the $\lambda_1/\lambda_2$ ratio.

5. The force amplifier of claim 2, wherein the first and second threads have respective outer diameters, the outer diameter of the first outer thread of the non-locking screw being either smaller than, larger than or equal to the outer diameter of the second thread of the self-locking screw.

6. The force amplifier of claim 1, wherein the compliant component is a compression spring.

7. The force amplifier of claim 1, wherein the compliant component is a telescopic component comprising:
inner and outer elements one of which is coupled to the non-locking screw and the other coupled to the locking screw so that the inner and outer elements are slidable towards one another in response to the axial input force;
an extension spring positioned between the inner and outer elements to bias the elements apart from each other in response to the axial input force; and
a ratchet mechanism between the non-locking screw and the one of the elements, wherein the extension spring provides a continuous contact between the non-locking screw and the one element upon removing the axial input force.

8. The force amplifier of claim 1, wherein the locking screw has two segments, an outer surface of one segment including a threaded portion and an outer surface of the other segment having a smooth outer surface, the segments being resiliently biased away from one another to urge the one segment against the second threaded region of the guide while the locking screw spirally moves towards a distal end of the guide track, the segments being displaceable towards one another in response to an external force so as to release the one segment from engagement with the guide track and displace the locking elements towards a proximal end of the guide track.

* * * * *